(12) United States Patent
Schmiege et al.

(10) Patent No.: US 10,323,054 B2
(45) Date of Patent: Jun. 18, 2019

(54) PRECURSORS FOR DEPOSITION OF METAL, METAL NITRIDE AND METAL OXIDE BASED FILMS OF TRANSITION METALS

(71) Applicant: Applied Materials, Inc., Santa Clara, CA (US)

(72) Inventors: Benjamin Schmiege, Santa Clara, CA (US); Jeffrey W. Anthis, San Jose, CA (US); David Thompson, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/823,755

(22) Filed: Nov. 28, 2017

(65) Prior Publication Data

US 2018/0148466 A1     May 31, 2018

Related U.S. Application Data

(60) Provisional application No. 62/427,129, filed on Nov. 28, 2016.

(51) Int. Cl.
| | |
|---|---|
| *C07F 15/06* | (2006.01) |
| *C07F 5/00* | (2006.01) |
| *C07F 15/04* | (2006.01) |
| *C07F 15/02* | (2006.01) |

(52) U.S. Cl.
CPC ............. *C07F 15/045* (2013.01); *C07F 5/00* (2013.01); *C07F 15/025* (2013.01); *C07F 15/06* (2013.01)

(58) Field of Classification Search
CPC ...... C07F 15/045; C07F 15/025; C07F 15/06; C07F 5/00
See application file for complete search history.

(56) References Cited

U.S. PATENT DOCUMENTS

| | | |
|---|---|---|
| 2004/0215030 A1 | 10/2004 | Norman |
| 2009/0208670 A1 | 8/2009 | Thompson et al. |
| 2012/0107502 A1 | 5/2012 | Thompson et al. |

FOREIGN PATENT DOCUMENTS

WO     2017/218460 A1     12/2017

OTHER PUBLICATIONS

Klaus et al., 689(23) J. Organometallic Chem. 3685-3700 (2004) (CAS Abstract) (Year: 2004).*
Caro, Catherine F, et al., "Review of metal 1-azaallyl complexes", Coordination Chemistry Reviews 219-221 (2001), pp. 605-663.
Cui, Chunming , et al., "Synthesis and characterization of 1-aza-allyl complexes of aluminum, gallium and bismuth", Polyhedron 19 (2000), Article: 3365, pp. 471-474.
Dube, Abhishek , et al., "Covalent Attachment of a Transition Metal Coordination Complex to Functionalized Oligo (phenyleneethynylene) Self-Assembled Monolayers", J. Am. Chem. Soc. 2005, 127, pp. 14299-14309.
Hitchcock, Peter B., et al., "Organometallic chemistry of the actinides. Part 3 Novel 1-aza-allyl- and β-diketiminatothorium chlorides; X-ray structures of [{Th(LL') 2 (μ3-Cl) (μ-Cl) 2 K( OEt 2)}] and[Th(LL)2 Cl 2 ] [LL'=N( SiMe)3 C( But) C( H) SiMe3 ; LL={N( SiMe3) C( Ph)}2 CH]1", Journal of Organometallic Chemistry 536-537 (1997), pp. 473-480.
Hitchcock, Peter B., et al., "Synthesis, characterization and reactions of 1,3-bis(trimethylsilyl)-1-aza-allyl-anthanide complexes; X-ray structures of [Sm( LL')2 l(thf)], [Yb( LL') 2] and [RN=C(But) CH(R)]2 (thf=tetrahydiofuran, LL'=η3-N(R)C(But)CHR, R=,SiMe3)", Journal of Organometallic Chemistry 549 (1997), pp. 1-12.
Hitchcock, Peter B., et al., "Variation of bonding modes in homoleptic tin(II) 1-azaallyls", Chem. Commun., 1997, pp. 1189-1190.
Leung, Wing-Por , et al., "Synthesis and structural characterisation of low-valent Group 14 metal complexes containing tridentate 2,6-pyridyl-bridged bis(1-azaallyl) ligands", Dalton Trans., 2003, pp. 1505-1508.
PCT International Search Report and Written Opinion in PCT/US2017/063355 dated Feb. 26, 2018, 14 pages.

* cited by examiner

*Primary Examiner* — Timothy R Rozof
(74) *Attorney, Agent, or Firm* — Servilla Whitney LLC

(57) ABSTRACT

Metal coordination complexes comprising a metal atom coordinated to at least one aza-allyl ligand having the structure represented by:

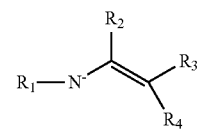

where each R1-R4 are independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens. Methods of depositing a film using the metal coordination complex and a suitable reactant are also described.

18 Claims, No Drawings

PRECURSORS FOR DEPOSITION OF METAL, METAL NITRIDE AND METAL OXIDE BASED FILMS OF TRANSITION METALS

CROSS-REFERENCE TO RELATED APPLICATIONS

This application claims priority to U.S. Provisional Application No. 62/427,129, filed Nov. 28, 2016, the entire disclosure of which is hereby incorporated by reference herein.

TECHNICAL FIELD

The present disclosure relates generally to methods of depositing thin films. In particular, the disclosure relates aza-allyl precursors and methods of depositing films.

BACKGROUND

In recent years, a greater portion of the elements in the periodic table are used at some point in a semiconductor or microelectronics device. For example, cobalt and cobalt based films have seen wider adoption for semiconductor and microelectronic applications. However, chemical vapor deposition (CVD) and atomic layer deposition (ALD) precursors have generally poor thermal stability or require additional processing steps to remove carbon contamination.

Therefore, there is a need in the art for metal precursors that have good thermal stability and form low carbon contaminated films.

SUMMARY

One or more embodiments of the disclosure are directed to metal coordination complexes comprising a metal atom coordinated to at least one aza-allyl ligand having a structure represented by:

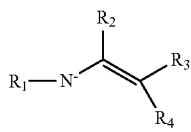

where each R1-R4 is independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens.

Additional embodiments of the disclosure are directed to metal coordination complexes having the general structure:

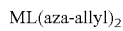

ML(aza-allyl)$_2$ where M is cobalt, L is a neutral donor ligand and aza-allyl has a structure represented by

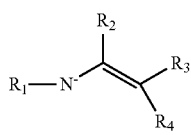

where each R is independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens.

Further embodiments of the disclosure are directed to processing methods comprising exposing a substrate surface to a metal precursor and a reactant to deposit a film on the substrate surface. The metal precursor comprises a metal coordination complex with a metal atom coordinated to at least one aza-allyl ligand having the structure represented by:

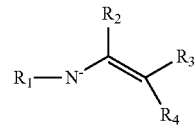

where each R1-R4 are independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

A "substrate" as used herein, refers to any substrate or material surface formed on a substrate upon which film processing is performed during a fabrication process. For example, a substrate surface on which processing can be performed include materials such as silicon, silicon oxide, strained silicon, silicon on insulator (SOI), carbon doped silicon oxides, amorphous silicon, doped silicon, germanium, gallium arsenide, glass, sapphire, and any other materials such as metals, metal nitrides, metal alloys, and other conductive materials, depending on the application. Substrates include, without limitation, semiconductor wafers. Substrates may be exposed to a pretreatment process to polish, etch, reduce, oxidize, hydroxylate, anneal, UV cure, e-beam cure and/or bake the substrate surface. In addition to film processing directly on the surface of the substrate itself, in the present invention, any of the film processing steps disclosed may also be performed on an underlayer formed on the substrate as disclosed in more detail below, and the term "substrate surface" is intended to include such underlayer as the context indicates. Thus for example, where a film/layer or partial film/layer has been deposited onto a substrate surface, the exposed surface of the newly deposited film/layer becomes the substrate surface.

Embodiments of the disclosure are directed to a new class of metal (e.g., La or Co) precursors that incorporate aza-allyl ligands. Formula (1) shows the general structure of an aza-allyl ligand which can be used with various embodiments of the disclosure. Some embodiments of the disclosure are directed to metal coordination complexes comprising a metal atom coordinated to at least one ligand having the structure represented by Formula (1):

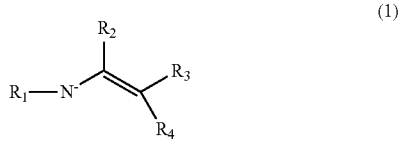

(1)

where each R1-R4 are independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens. In some embodiments, none of the R1-R4 groups comprises a silyl group.

In some embodiments, the R1 group is a hydrogen atom. In some embodiments, the R1 group is a branched or unbranched C1-C6 alkyl group.

In some embodiments, the R2 group is not a hydrogen atom. It has been found that increasing the size of the R2 group may increase the thermal stability of the metal complex. In one or more embodiments, the R2 group is a branched or unbranched C1-C6 alkyl group.

In some embodiments, neither the R3 or R4 groups are hydrogen atoms. In some embodiments, the R3 and R4 groups are the same group. In some embodiments, the R3 group is different from the R4 group. In some embodiments, one of the R3 or R4 groups is hydrogen and the other of the R3 and R4 group is a branched or unbranched C1-C6 alkyl group.

In some embodiments, any or all of R1 to R4 comprises a $NR_2$ group, where each R of the $NR_2$ is independently selected from H, branched or unbranched C1-C6 alkyl. In some embodiments, one of the R groups of the $NR_2$ is hydrogen and the other is a branched or unbranched C1-C6 alkyl. In some embodiments, both of the R groups of the $NR_2$ are branched or unbranched C1-C6 alkyl groups. In one or more embodiments, both of the R groups of the $NR_2$ are the same group.

The aza-allyl ligands of some embodiments have a base structure of N—C=C with substituents on each of the base atoms that can be H, branched or unbranched alkyl groups, alkenyl groups, alkynyl groups, cycloalkyl groups having in the range of 1 to 6 carbon atoms, silyl groups and halogens. In some embodiments, one or two of the R groups is an alkyl group with 4 or 5 carbon atoms and the other R groups are hydrogen. In one or more embodiments, one or two of the R groups are trimethylsilyl groups and the other R groups are hydrogen. In some embodiments, one or two R groups are trifluormethyl groups and the other R groups are hydrogen.

Without being bound by any particular theory of operation, it is believed that the ligand is mono-anionic and is able to bond to the metal atom through an $\eta^1$-N and $\eta^2$-CC bonding mode.

In some embodiments, two, three or four ligands bond to each metal atom. The compounds can be homoleptic (all of the ligands are the same) or heteroleptic (different ligands). In one or more embodiments, the lanthanum atom exists in an equilibrium with the $\eta^1$-C and $\eta^2$-CN bonding modes.

In some embodiments, the compound is heteroleptic and at least one ligand is a neutral donor ligand. Suitable neutral donor ligands include, but are not limited to, CO, alkenes, alkynes that bond in an $\eta^2$ manner, phosphines and amines. In one or more embodiments, the compound has a cobalt atom with two aza-allyl ligands and one CO neutral donor ligand.

The metal can be any suitable metal including any of the cobalt, lanthanides, yttrium or scandium. In some embodiments, the metal is selected from the group consisting of Co, La, Ce, Pr, Nd, Pm, Sm, Eu, Gd, Tb, Dy, Ho, Er, Tm, Yb, Lu, Y, Sc and combinations thereof. Examples and embodiments may be discussed with regard to the lanthanum atom; however, those skilled in the art will understand that this is merely exemplary and should not be taken as limiting the scope of the disclosure.

Without being bound by any particular theory of operation, it is believed that the bonding of aza-allyl with lanthanides is consistent with Scheme 2.

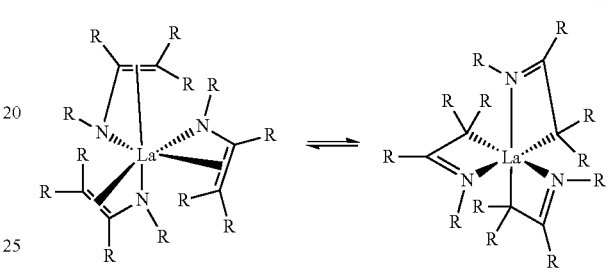

(2)

In use as an atomic layer deposition or chemical vapor deposition precursor, a suitable compound may be reacted with the aza-allyl precursor. In a chemical vapor deposition (CVD) process, the aza-allyl precursor and the coreactant are allowed to mix and react in the gas phase to deposit on the surface of the substrate.

In an atomic layer deposition (ALD) process, the aza-allyl precursor and the co-reactant are flowed separately into the process chamber, or flowed into separate isolated sections of the process chamber to prevent or minimize any gas phase reactions. In the ALD process, the aza-allyl precursor is allowed to chemisorb or react with the substrate surface, or a material on the substrate surface. The co-reactant can then react with the chemisorbed aza-allyl to form the target film. In and ALD reaction, the precursor and co-reactant are sequentially exposed to the substrate surface; meaning that one of the precursor and co-reactant is exposed to the substrate surface (or portion of the substrate surface) at any time.

Suitable co-reactants include, but are not limited to, hydrogen, ammonia, hydrazine, hydrazine derivatives, oxygen, ozone, water, peroxide, combinations and plasmas thereof. In some embodiments, the co-reactant comprises one or more of $NH_3$, hydrazine, hydrazine derivatives, $NO_2$, combinations thereof, plasmas thereof and/or nitrogen plasma to deposit a metal nitride film (e.g., $La_xN_y$ or $Co_xN_y$). In some embodiments, the co-reactant comprises one or more of $O_2$, $O_3$, $H_2O_2$, water, plasmas thereof and/or combinations thereof to deposit a metal oxide film (e.g., LaxOy). In some embodiments, the coreactant comprises one or more of $H_2$, hydrazine, combinations thereof, plasmas thereof, argon plasma, nitrogen plasma, helium plasma, $Ar/N_2$ plasma, Ar/He plasma, $N_2$/He plasma and/or $Ar/N_2$/He plasma to deposit a metal film (e.g., La or Co).

Some embodiments of the disclosure are directed to lanthanum precursors and methods of depositing lanthanum containing films. The lanthanum containing films of some embodiments comprises one or more of lanthanum metal, lanthanum oxide, lanthanum nitride, lanthanum carbide, lanthanum boride, lanthanum oxynitride, lanthanum oxycarbide, lanthanum oxyboride, lanthanum carbonitride, lanthanum borocarbide, lanthanum oxycarbonitride, lanthanum oxyboronitride and/or lanthanum oxyborocarbonitride. Those skilled in the art will understand that the film deposited may have a nonstoichiometric amount of metal, oxygen, nitrogen, carbon and/or boron atoms on an atomic basis. Boron and/or carbon atoms can be incorporated from the metal precursor or the reactant.

Some embodiments of the disclosure are directed to cobalt precursors and methods of depositing cobalt containing films. The cobalt containing films of some embodiments comprises one or more of cobalt metal, cobalt oxide, cobalt nitride, cobalt carbide, cobalt boride, cobalt oxynitride, cobalt oxycarbide, cobalt oxyboride, cobalt carbonitride, cobalt borocarbide, cobalt oxycarbonitride, cobalt oxyboronitride and/or cobalt oxyborocarbonitride. Those skilled in the art will understand that the film deposited may have a nonstoichiometric amount of metal, oxygen, nitrogen, carbon and/or boron atoms on an atomic basis. Boron and/or carbon atoms can be incorporated from the metal precursor or the reactant.

Some embodiments of the disclosure are directed to metal coordination complexes having the general structure $ML(aza-allyl)_2$, where M is a cobalt, L is a neutral donor ligand and aza-allyl has a structure represented by

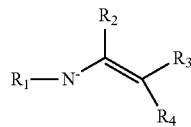

where each R is independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens. In some embodiments, the neutral donor ligand comprise CO.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or it can be moved from the first chamber to one or more transfer chambers, and then moved to the separate processing chamber. Accordingly, the processing apparatus may comprise multiple chambers in communication with a transfer station. An apparatus of this sort may be referred to as a "cluster tool" or "clustered system," and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present invention are the Centura® and the Endura®, both available from Applied Materials, Inc., of Santa Clara, Calif. However, the exact arrangement and combination of chambers may be altered for purposes of performing specific steps of a process as described herein. Other processing chambers which may be used include, but are not limited to, cyclical layer deposition (CLD), atomic layer deposition (ALD), chemical vapor deposition (CVD), physical vapor deposition (PVD), etch, pre-clean, chemical clean, thermal treatment such as RTP, plasma nitridation, degas, orientation, hydroxylation and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions, and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants. According to one or more embodiments, a purge gas is injected at the exit of the deposition chamber to prevent reactants from moving from the deposition chamber to the transfer chamber and/or additional processing chamber. Thus, the flow of inert gas forms a curtain at the exit of the chamber.

The substrate can be processed in single substrate deposition chambers, where a single substrate is loaded, processed and unloaded before another substrate is processed. The substrate can also be processed in a continuous manner, similar to a conveyer system, in which multiple substrate are individually loaded into a first part of the chamber, move through the chamber and are unloaded from a second part of the chamber. The shape of the chamber and associated conveyer system can form a straight path or curved path. Additionally, the processing chamber may be a carousel in which multiple substrates are moved about a central axis and are exposed to deposition, etch, annealing, cleaning, etc. processes throughout the carousel path.

During processing, the substrate can be heated or cooled. Such heating or cooling can be accomplished by any suitable means including, but not limited to, changing the temperature of the substrate support and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated continuously or in discreet steps. For example, a substrate may be rotated throughout the entire process, or the substrate can be rotated by a small amount between exposures to different reactive or purge gases. Rotating the substrate during processing (either continuously or in steps) may help produce a more uniform deposition or etch by minimizing the effect of, for example, local variability in gas flow geometries.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A metal coordination complex comprising a metal atom coordinated to two or three aza-allyl ligands, each aza-allyl ligand having a structure represented by:

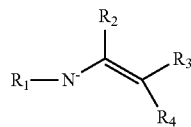

wherein each R1-R4 is independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens, and wherein the metal atom is selected from the group consisting of Co, La, Ce, Pr, Nd, Pm, Sm, Eu, Gd, Tb, Dy, Ho, Er, Tm, Yb, Lu, Y, Sc and combinations thereof.

2. The metal coordination complex of claim 1, wherein each of R1-R4 are independently selected from H and branched or unbranched C1-C6 alkyl groups.

3. The metal coordination complex of claim 1, wherein one or two of R1-R4 comprises an alkyl group having 4 or 5 carbon atoms.

4. The metal coordination complex of claim 1, wherein none of R1-R4 is a silyl group.

5. The metal coordination complex of claim 1, wherein one or two of R1-R4 comprises a trifluoromethyl group.

6. The metal coordination complex of claim 1, wherein the metal atom comprises Co.

7. The metal coordination complex of claim 6, wherein there are two aza-allyl ligands and a neutral electron donor ligand.

8. A metal coordination complex having the general structure:

$$ML(aza\text{-}allyl)_2$$

where M is cobalt, L is a neutral donor ligand and aza-allyl has a structure represented by

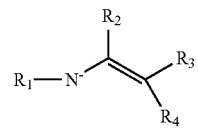

wherein each R1-R4 is independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens.

9. The metal coordination complex of claim 8, wherein each of R1-R4 is independently selected from the group consisting of H and branched or unbranched C1-C6 alkyl groups.

10. The metal coordination complex of claim 8, wherein the neutral donor ligand comprises CO.

11. A processing method comprising exposing a substrate surface to a metal precursor and a reactant to deposit a film on the substrate surface, the metal precursor comprising a metal coordination complex with a metal atom coordinated to two or three aza-allyl ligands, each aza-allyl ligand having a structure represented by:

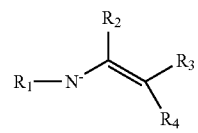

where each R1-R4 are independently selected from the group consisting of H, branched or unbranched C1-C6 alkyl, branched or unbranched C1-C6 alkenyl, branched or unbranched C1-C6 alkynyl, cycloalkyl groups having in the range of 1 to 6 carbon atoms, silyl groups and halogens, and wherein the metal atom is selected from the group consisting of Co, La, Ce, Pr, Nd, Pm, Sm, Eu, Gd, Tb, Dy, Ho, Er, Tm, Yb, Lu, Y, Sc and combinations thereof.

12. The processing method of claim 11 wherein the metal atom comprises Co.

13. The processing method of claim 12, wherein the metal coordination complex is homoleptic.

14. The processing method of claim 12, wherein the metal coordination complex has two aza-allyl ligands and a neutral donor ligand.

15. The processing method of claim 11, wherein the reactant comprises one or more of $NH_3$, hydrazine, hydrazine derivatives, $NO_2$, combinations thereof, plasmas thereof or nitrogen plasma to deposit an metal nitride film.

16. The processing method of claim 11, wherein the reactant comprises one or more of $O_2$, $O_3$, $H_2O_2$, water, plasmas thereof or combinations thereof to deposit a metal oxide film.

17. The processing method of claim 11, wherein the co-reactant comprises one or more of $H_2$, hydrazine, combinations thereof, plasmas thereof, argon plasma, nitrogen plasma, helium plasma, $Ar/N_2$ plasma, Ar/He plasma, $N_2$/He plasma or $Ar/N_2$/He plasma to deposit a metal film.

18. The processing method of claim 11, wherein the metal precursor and the reactant are exposed to the substrate surface sequentially.

\* \* \* \* \*